(12) United States Patent
Erens et al.

(10) Patent No.: US 10,989,354 B2
(45) Date of Patent: Apr. 27, 2021

(54) SUSPENSION SYSTEM AND BRAKE DEVICE AND ROTATION LIMITING DEVICE FOR USE IN THE SUSPENSION SYSTEM

(71) Applicant: IHB B.V., Zwolle (NL)

(72) Inventors: Roderik Gerrit Frederik Erens, Brummen (NL); Cornelis Bassa, Leusden (NL); Johannes Antonius Maria Grimberg, Bornerbroek (NL)

(73) Assignee: IHB B.V., Zwolle (NL)

( * ) Notice: Subject to any disclaimer, the term of this patent is extended or adjusted under 35 U.S.C. 154(b) by 0 days.

(21) Appl. No.: 15/929,234

(22) Filed: Feb. 26, 2020

(65) Prior Publication Data
US 2020/0278080 A1 Sep. 3, 2020

(30) Foreign Application Priority Data
Mar. 1, 2019 (NL) .................................. 2022662

(51) Int. Cl.
| | | |
|---|---|---|
| F16M 13/02 | (2006.01) | |
| A61B 90/35 | (2016.01) | |
| A61B 90/00 | (2016.01) | |
| A61B 90/50 | (2016.01) | |
| F16C 11/04 | (2006.01) | |
| F16D 49/08 | (2006.01) | |
| F16D 65/18 | (2006.01) | |
| F21V 21/26 | (2006.01) | |
| G03B 17/56 | (2021.01) | |
| F16D 121/24 | (2012.01) | |

(52) U.S. Cl.
CPC ........... *F16M 13/027* (2013.01); *A61B 90/35* (2016.02); *A61B 90/361* (2016.02); *A61B 90/37* (2016.02); *A61B 90/50* (2016.02); *F16C 11/04* (2013.01); *F16D 49/08* (2013.01); *F16D 65/18* (2013.01); *F16M 13/022* (2013.01); *F21V 21/26* (2013.01); *G03B 17/561* (2013.01); *F16D 2121/24* (2013.01); *F16M 2200/022* (2013.01)

(58) Field of Classification Search
USPC ......................................... 248/555
See application file for complete search history.

(56) References Cited

U.S. PATENT DOCUMENTS

| | | | | |
|---|---|---|---|---|
| 7,837,674 | B2 * | 11/2010 | Cooper ................. | A61B 34/71 606/1 |
| 9,291,793 | B2 * | 3/2016 | Cooper ................ | B25J 19/0016 |
| 9,605,800 | B2 * | 3/2017 | Huang .................. | A61B 90/50 |
| 10,041,625 | B2 * | 8/2018 | Volkenand ........... | A61G 13/107 |
| 10,682,190 | B2 * | 6/2020 | Griffiths ................ | A61B 34/32 |

(Continued)

*Primary Examiner* — Monica E Millner

(74) *Attorney, Agent, or Firm* — Oppedahl Patent Law Firm LLC

(57) ABSTRACT

The invention relates to a suspension system, or pendant unit, intended for attachment to an upper structure at a selectable height for suspending a load wherein the load may comprise a carrier for the one or more medical devices or one or more devices, such as for instance a (target) lighting, monitor, camera or a medical device.

The problem of the known suspension system is that during the entire repositioning the user has to react on the behavior of the system due to a variety of internal and external forces. It is an object of the invention to provide an alternative suspension system for the known suspension system wherein this problem is addressed.

17 Claims, 10 Drawing Sheets

(56) References Cited

U.S. PATENT DOCUMENTS

| | | | |
|---|---|---|---|
| 10,710,246 B2* | 7/2020 | McGrogan | B25J 15/0028 |
| 10,766,138 B2* | 9/2020 | Perplies | B25J 9/1674 |
| 2007/0156122 A1* | 7/2007 | Cooper | A61B 90/50 |
| | | | 606/1 |
| 2013/0338430 A1* | 12/2013 | Volkenand | A61M 21/02 |
| | | | 600/28 |
| 2016/0296297 A1 | 10/2016 | Perplies | |
| 2017/0112580 A1* | 4/2017 | Griffiths | A61B 34/35 |
| 2017/0341232 A1 | 11/2017 | Perplies | |
| 2018/0296285 A1* | 10/2018 | Simi | G05B 19/402 |
| 2019/0145473 A1* | 5/2019 | Puterbaugh | A61B 90/50 |
| | | | 188/218 R |
| 2019/0192238 A1* | 6/2019 | Tsuboi | B25J 9/06 |

* cited by examiner

SUSPENSION SYSTEM AND BRAKE DEVICE AND ROTATION LIMITING DEVICE FOR USE IN THE SUSPENSION SYSTEM

The invention relates to a suspension system, or pendant unit, intended for attachment to an upper structure at a selectable height for suspending a load wherein the load may comprise a carrier for the one or more medical devices or one or more devices, such as for instance a (target) lighting, monitor, camera or a medical device, comprising
- a fastening member for attachment to the upper structure,
- one or more articulated arms comprising a system of one main arm and at least one carrier arm, in which
  - the proximal end of the main arm is connected to the fastening member by means of a first rotation connection, which first rotation connection comprises a first axis of rotation for rotating the main arm about the first axis of rotation and in a first plane of rotation, wherein, in use of the suspension system, the longitudinal direction of the first axis of rotation preferably makes an angle of substantially 90° with the longitudinal plane of the upper structure;
  - the first rotation connection is provided with an electronically operable first brake device for braking the rotation of the main arm relative to the first axis of rotation;
  - the proximal end of the carrier arm is connected to the distal end of the main arm by means of a second rotation connection, which second rotation connection comprises a second axis of rotation for rotating the carrier arm about the second axis of rotation and in a second rotation plane, wherein, in use of the suspension system, the longitudinal direction of the second axis of rotation preferably runs parallel to the longitudinal direction of the first axis of rotation;
  - the second rotation connection is provided with an electronically operable second brake device for braking the rotation of the carrier arm relative to the second axis of rotation;
  - the carrier arm is arranged for attaching the load to the distal end thereof;
- a first control device for controlling the first and second brake device.

A suspension system according to the preamble is known in the state of the art. The known suspension system is described in the US patent application US2017/0341232A1. The known suspension system is used in operation rooms for locally moving medical devices. The object of the known suspension system is to provide a suspension system wherein the articulated arms can be moved in an operating room in a particularly simple or flexible manner without much attention from the operator. The first control device of the known system comprises a sensor device to detect an external force acting on or applied to the suspension system, wherein the first control device is configured to control each of the brake devices as a function of the measured value, in particular, to release it and adjust the degree of freedom of movement.

The problem of the known suspension system is that during the entire repositioning the user has to react on the behavior of the system due to a variety of internal and external forces. Differences in mass, speed and system geometry make it difficult to clarify the intentions of the user based on measured forces on the system. Many times the pendant-unit will not move in the desired direction, in line with the intuitive push or pull by an operator. Rotation capabilities of the main arm and carrier arm combination do not support the ideal path to the desired position. This is influenced by system parameters, the position of the carrier arm related to the main arm and the direction of the repositioning force at the end of the carrier arm.

It is an object of the invention to provide an alternative suspension system for the known suspension system wherein this problem is addressed.

SUMMARY OF THE INVENTION

The suspension system according to the invention provides in a suspension system according to the preamble characterizing in that
- the suspension system comprises first measuring means for measuring a movement of the articulated arm wherein the first measuring means are arranged for measuring a first rotation of the main arm about the first axis of rotation relative to a predetermined point on the first axis of rotation and measuring a second rotation of the carrier arm about the second axis of rotation with respect to a predetermined point on the second axis of rotation;
- the first brake device is controllable by means of an adjustable first brake moment, which is dynamically determined during the rotation of the articulated arm;
- the second brake device is controllable by means of an adjustable second brake moment which is dynamically determined during the rotation of the articulated arm;
- the first control device is arranged to dynamically calculate the desired first brake moment and the desired second brake moment on the basis of the actual rotations and geometry of the articulated arm, in which the relationship between the rotations of the articulated arm and the first brake moment as well as the second brake moment is predetermined;
- the first control device is adapted to control the first brake device and the second brake device to the calculated first and second brake moment respectively wherein, in use of the suspension system, the actual first brake moment and actual second brake moment are such that a user will have to exert a(n) (adjustable) minimum displacement force on the load for the initial movement of the load irrespective of the actual rotation position of the main arm and/or the carrier arm;
- the first control device is adapted to set the actual first brake moment and the actual second brake moment in stationary state always larger or equal than an adjustable predetermined minimum moment of movement in use of the suspension system.

The characterizing features provide in a suspension system which enables a controlled rotation behavior of the articulated arm by dynamically adjusting the friction of each brake device such that the operator can reposition the load in a smooth manner in any direction and whatever the position of the articulated arm. Instead of measuring an external force exerted by an operator and acting on the load, such as in the known suspension system, the suspension system according to the invention adjust the frictional parameters of the first and second brake device depending on the geometry and rotation of the articulated arm, therefore enabling a natural movement over the path of travel of the load.

Preferably the suspension system has three modes of operation, which are a stationary mode, a move mode and a hold mode.

In the stationary mode the articulated arm is not moving. The first and second brake devices are activated in order to prevent undesired moving and/or drifting of the load. The brake friction of the first and second brake device is a function of the orientation and geometry of the main arm and the carrier arm. The brake friction of the first brake device is higher in the stretched position of the articulated arm. The brake friction of the first brake device is lower in case the carrier arm is straight under the upper arm.

In the move mode the operator is pushing against the load and the articulated arm has to follow the direction the load is pushed. The first and second brake devices are activated in order to dynamically adjust the brake friction as a function of the rotation and geometry of the main arm and carrier arm, such that the effort is low to reposition the load in any direction and does not depend on the rotational angles of the main arm and carrier arm.

In the hold mode the aim of the operator is to lock the position of the load thereby holding the articulated arm in its actual position and prevent any unintended movement. Preferable the suspension system according to the invention can be arranged with a user activated button to set the brake friction of the first and second brake device to a high value.

In a preferred embodiment of the suspension system the first control device is arranged for determining the desired first brake moment for stationary placement of the load in the stationary mode, wherein the desired first brake moment is proportional with the first formula:

$$M_{main\ arm,stat} \sim \frac{(F_{min} \times L_{carrier\ arm} \times \sin(\beta))}{\sin\left(arctg\left(\frac{L_{carrier\ arm} \times \sin(\beta)}{L_{main\ arm} + L_{carrier\ arm} \times \cos(\beta)}\right)\right)}$$

and arranged for determining the desired second brake moment for stationary placement of the load, wherein the desired second brake moment is proportional with the second formula:

$$M_{carrier\ arm,stat} \sim (F_{min} \times L_{carrier\ arm}) \times Adj(\beta)$$

wherein:

| | |
|---|---|
| $M_{main\ arm,\ stat}$ | = Desired first brake moment main arm at stationary placement of load |
| $M_{carrier\ arm,\ stat}$ | = Desired second brake moment carrier arm at stationary placement of load |
| $F_{min}$ | = Adjustable minimum displacement force for initial movement of the load |
| $L_{carrier\ arm}$ | = Length of the carrier arm |
| $L_{main\ arm}$ | = Length of the main arm |
| $\beta$ | = angle between a longitudinal direction of the main arm and the carrier arm near the second rotation connection or axis; |
| $Adj(\beta)$ | = Dynamic adjusting function based on position of the carrier arm ($\beta$) to compensate for drift |

Preferably, the brake moment of each of first and second rotation in the articulated arm have a known relation to the force applied on the brakes of the brake device in order to set the brake friction. Therefore the suspension system according to the invention is able to set the brake friction of each of the brake devices depending on the calculated desired brake moment at the rotation connection of each arm. The said formulas ensure that the articulated arm will not drift out of position. Also it ensures that the load (medical device(s)) can be used without an undesired replacement of the articulated arm. Furthermore, it ensures that the articulated arm can be moved to another position with minimal effort by the operator.

In a further preferred embodiment of the suspension system according to the invention the first control device is arranged for controlling the first brake device in move mode, wherein the desired first brake moment is proportional with the third formula:

$$M_{main\ arm,move} \sim M_{main\ arm,stat} \times C(\ )$$

and arranged for controlling the second brake device in move mode wherein the desired second brake moment is proportional with the fourth formula:

$$M_{carrier\ arm,move} \sim M_{carrier\ arm,stat} \times D(\ )$$

wherein $0 < C(\ ), D(\ ) < 1$ and

| | |
|---|---|
| $M_{main\ arm,\ move}$ | = Desired first brake moment main arm when moving the load |
| $M_{carrier\ arm,\ move}$ | = Desired second brake moment carrier arm when moving the load |
| $C(\ ), D(\ )$ | = Dynamic control function depending on the state, arm positions and rotation speed of the articulated arm |

The above mentioned technical features solve the problem in known suspension system that it is nearly impossible to move the load out of position when the main arm and the carrier arm lie in line with each other. In the inventive suspension system the brake moment of the main arm, and therefore the brake friction of the first brake device is much higher than the brake moment of the carrier arm and subsequently the brake friction of the second brake device. The carrier arm therefore continues to be rotatable, while the operator has the experience that he/she can move the load in an easy manner in the intended direction.

Preferably the parameters C( ) and D( ) have the following values in the different states:
  stationary placement of the articulated arm: C( ), D( )=1;
  moving of the articulated arm by the operator: 0<C( ),D( )<1;
  locking the articulated arm: 1<C( ),D( )<max, wherein max sets the brake moment to a maximum value.
  during unexpected external impacts and control actions to avoid or bypass predicted collisions; C( ),D( )≠1

Preferably the first measuring means comprise one or more accelerometers to help identify a transition of the state (stable, move, hold) of the suspension system.

Preferably the first measuring means comprises the following means for measuring the angle of rotation and the direction of rotation in a rotation connection:
  a first and second magnetic encoder ring which are placed in a fixed position on a tubular part of the rotation connection;
  two magnetic field sensors, such as a hall sensor, which are placed at a surrounding part of the rotation connection and positioned at a circumferential side of the magnetic rings;
  the first magnetic encoder ring is provided with proportional distributed magnetic markers for determining the relative angular rotation of the rotation part by means of keeping track of markers using the first magnetic field sensor;
  the second magnetic encoder ring in the circumference is provided with a disproportional pattern of magnetic markers for determining the absolute position of the relevant arm relative to the rotation axis by means of one-off detection of a part of the pattern with the aid of the second magnetic field sensor;
  the magnetic rings and magnetic field sensors encounter a relative displacement during rotation;

This allows for determining the exact orientation and positioning of the main arm and carrier arm in relation to their axes and to each other.

In a further preferred embodiment of the suspension system according to the invention, the carrier arm near the proximal end is provided with a fourth rotation connection, which fourth rotation connection comprises a fourth rotation axis for rotating the carrier arm about the fourth rotation axis in a fourth rotation plane, which third plane of rotation in use is perpendicular to the longitudinal plane of the upper structure;

the first measuring means are arranged for measuring a fourth rotation of the carrier arm about the fourth axis of rotation relative to a predetermined point on the fourth axis of rotation;

the first control device is arranged to predict a collision between the carrier arm and the main arm;

the first control device is arranged to control the second brake moment and/or disabling the up/down movement of the carrier arm (in case the fourth rotation connection is motorized) in a predicted collision between the main arm and the carrier arm in order to prevent the predicted collision.

In a further preferred embodiment of the suspension system according to the invention, the first measuring means are arranged for measuring an acceleration of the distal end of the carrier arm which can for example be caused by an impact.

The load is connected to the distal end of the carrier arm by means of a third rotation connection with a fourth axis of rotation, around which the load can rotate, wherein the fourth axis is parallel to the first and second axis of rotation.

The length of the main arm is generally defined as the distance between the first and second axis of rotation.

The length of the carrier arm is generally defined as the distance between the second axis and the fourth axis of rotation.

The measuring of the fourth rotation is preferably derived from measurements performed by an accelerometer which is preferably located on the distal end of the carrier arm.

In general the articulated arm can experience an impact,
a). when the articulated arm and/or the load bumps (in move mode) against an object;
b). when another object bumps against the articulated arm and/or the load.

The first control device is preferable arranged to detect such an impact using the measured values from the accelerometer.

After detection of an impact in move mode the first control device is arranged to increase the brake moment of all rotation connections of the articulated arm to a high value. Subsequently, the suspension system is put in the stationary mode.

If an impact is detected in stationary mode of the suspension system, the first control device is arranged to either strongly increase or decrease the brake moment of all rotation connections depending on an stored parameter value, which is set during installation of the suspension system.

The detection of a sudden increase of the rotational speed of the articulated arm is defined as a speed swing, which can occur in a (emergency) situation when the operator pushed the articulated arm with the load uncontrolled and resolute from its current position.

In a further preferred embodiment of the suspension system according to the invention, the first control device comprises calculating means for calculating the displacement speed of the load in the move mode on the basis of the first measuring means, the first control device is arranged to detect the passing of a lower limit value of the speed of movement of the end of the carrier arm, in which the lower limit value is predetermined and the first control device is arranged to control the first brake moment and/or second brake moment on detection of the passing of the lower limit value in order to limit the distance travelled by the load to a predefined maximum distance after which the articulated arm is put in stationary mode.

On the basis of fixed data of the geometry of the main arm, carrier arm and load (which usually has a box or cylinder shape) combined with the current horizontal and vertical positions of the various system parts of the suspension system, the relevant first control device is calculate the current space used by the suspension system. By adding information about the current rotation speeds, the first control device is arranged to calculated what the (predicted) space use of the system will be between current and a certain moment in the future. The space in use by the individual parts of a suspension system (main arm+carrier arm+load) forms the space use of a pendant system. The allocated space use of the suspension system is expressed in a multidimensional matrix with a certain spatial resolution. The required dynamic data is collected using the available measuring means such as the rotation angle sensors on the horizontal rotation connections of the main arm relative to the fastening member and the carrier arm relative to the main arm, as well as information from e.g. the acceleration sensor on the vertical rotation connection of the carrier arm in case the carrier arm is height-adjustable. Additionally, the angle of rotation of the load relative to the carrier arm is also measured with a (horizontal) angle measuring device in a similar manner as to the other rotation connections.

In a further preferred embodiment of the suspension system according to the invention, the first control device is arranged to store spatial coordinates of one or more stationary objects in a space, the first control device is arranged to avoid a predicted collision of the main arm and/or the carrier arm base and/or the load with a stationary object, based on the predicted space allocation which is calculated using the information of the first measuring means and the first control device is arranged, in a predicted collision, to control the first brake moment and/or the second brake moment in order to prevent a collision between an object with the main arm and/or the carrier arm and/or the load.

In a further preferred embodiment of the suspension system according to the invention, the first control device is arranged for communication with one or more further suspension system according to the invention wherein the communication comprises information of the allocated space of the one or more further suspension system, the first control device is arranged for assessing the information for controlling the first and second brake device in order to prevent a collision between the main arm, carrier arm or load with the main arm, carrier arm or load of the further suspension system and vice versa.

As soon as the first control device determines that the (predicted) use of the suspension system will overlap with the space use of another suspension system, the first control device is arranged to control the desired brake moment when using the pendant unit (in move mode) of one or more rotation connections (with a brake device), so that the articulated arm will find another way within the available possibilities, or will stop the articulated arm if there are no other options available.

As soon as the first control device of a suspension system determines during stationary mode that the (predicted) use of another suspension system will have an overlap with the (current) allocated space of the suspension system of said first control device, the first control device will strongly increase or decrease the desired brake moment of the rotation connections based on a parameter specified at the installation of the suspension system, after which the stationary mode becomes active again.

In a further preferred embodiment of the suspension system according to the invention, the first and second rotation connection comprises a rotation limiting device with a first and/or second (physical) hard end stop for limiting the rotation between a first physical end angle (right rotation direction) and a second physical end angle (left rotation direction). The first control device is arranged for determining and storing the actual values of both physical end angles of each rotation connection. A soft-stop function is implemented at both physical end angles of the first and second rotation connection. The first control device is thereby arranged to activate the soft-stop function during move mode, in which the brake moment of the relevant brake device is controlled to prevent a collision with the related hard end stop. The soft-stop function has as a result that the rotation is stopped in a soft manner near the physical end angle, and the articulated arm is put in its stationary state.

Preferably, the first control device is also arranged to detect if a physical end stop has been removed. When a carrier arm or main arm is pushed over a (perceived) physical end angle by an operator, the first control device will deactivate the related soft-stop function. Hence, the first control device will no longer control the brake moment of the corresponding brake device at that position.

The first control device is also preferably arranged to register the two physical end angles of the first and second rotating connection in at least three ways:

a). manual input of the absolute rotation angles, preferably by a service operator during installation of the suspension system;

b). by placing the relevant arm in a known end stop position and register the measured rotation angle in the storing means during installation of the suspension system;

c). by using an auto end stop search function implemented in the first control device; after registering multiple impacts at a particular rotation angle when the main arm and/or carrier arm is moving in a particular direction, the first control device is arranged to store this particular rotation angle as an end stop in its storing means. The next time this rotation angle is reached by a carrier arm or main arm the articulated arm the soft stop function will be active on this rotation angle such that the arm is stopped in a soft controlled manner.

The invention also relate to a brake device for use in a suspension system according to the invention, wherein the brake device comprises an at least partially annular brake caliper, which caliper is intended for placement over a cylindrical shaped part of the first or second rotation connection, wherein the inner side of the brake caliper is being provided with a brake lining and the caliper can be operated by moving the ends of the at least partially annular caliper towards each other by means of a lever, in which the lever is operable by means of a controllable stepper motor and in which the lever is provided with a force sensor, and the force exerted on the lever has a predetermined relation with the brake moment of the brake device, and wherein the brake device comprises a second control device, which second control device comprises a feedback loop, in which the force sensor is arranged, such that the brake device can be controlled to a desired brake moment as set by the first control device.

Furthermore, the invention is also related to a rotation limiting device for use in a rotation connection of the suspension system according to the invention, which can also be used as an alternative limiting device for use in a rotation connection of a known suspension system.

The rotation limiting device according to the invention comprises a first rotation connection member and a second rotation connection member, each of which is adapted for further attachment to support the main arm, support arm, load, carrier or attachment member.

The first rotation connection member is at least provided with a cylindrical part, the second rotation connection member is at least provided with a round recess, in which the cylindrical shaped part is form fittingly arranged such that the first rotation connection member can rotate relative to the second rotation connection member about a common axis of rotation. The round recess of the second rotation connection member is provided with a groove on an inner surface thereof. The cylindrical shaped part and the groove form a hollow space between the first and second rotation connection member. The cylindrical shaped partis provided with a plurality of slots, in which each slot partially follows the circumferential direction of the cylindrical shaped part. Each slot is adapted to receive a first stop element, in which the first stop element extends into the hollow space and is displaceable in the slot during rotation of the first rotation connection member with respect to the second rotation connection member. The second rotation connection member comprises a stop element, in which the second stop element extends into the hollow space, wherein the rotation of the first rotation connection member with respect to the second rotation connection member in a first direction of rotation is limited by a cooperating first and second stop element, in which during rotation the second stop element positions itself against a first side of a first stop element and upon further rotation in the rotation direction the first stop element by means of the abutting second stop element moves further along the slot until a maximum displacement is reached after which further rotation is no longer possible.

The abovementioned technical features of the rotation limiting device according to the invention have the advantage that during rotation of the first rotation connection member relative to the second rotation connection member the second stop element will abut against the first stop element, after which the first stop element can further be displaced in the slot, thereby allowing further rotation until the first stop element has reached its maximum displacement.

In a first embodiment of the rotation limiting device according to the invention the first stop element is displaceable in the slot over a length of at least twice the width of the portion of the second stop element extending into the hollow space. These features allows a rotation, in case of a single first stop element and second stop element, over a minimum of 360°.

In a further embodiment of the rotation limiting device according to the invention the second rotation connection member is provided with an opening for detachable engagement of the second stop element, in which the opening extends from an outer side of the second rotation connection member to an inner side of the groove and the opening is arranged to pass the first stop element to a slot. These features allows for a convenient setting of the maximum rotation for a particular rotation direction by placing a first stop element in the correct slot through the opening in the second rotation connection member.

In a further embodiment of the rotation limiting device according to the invention the first stop element is spherical and the slot and the groove have an at least partially circular cross section for fitting the spherical stop element into the hollow space. These features allows for a movement of the first stop element in the slot with reduced friction.

Preferably the second stop element is pin-shaped and preferably arranged as a bolt, which can be screwed into the opening in the second rotation connection member.

Methods of Operation

During installation the control device will receive and store system parameters related to the configuration and geometry of the controlled suspension system (e.g effective length of the arms), its environment (e.g space allocation of stationary objects) and settings related to the desired behavior of the suspension system (e.g minimal effort for initial movement of the articulated arm).

Most of the time the suspension system will be in the stationary mode. In stationary mode, the optimal brake moments for the first and second rotation connection are dynamically defined by the first control device based on the measured positions of the main arm and carrier arm in order to avoid drifting of the articulated arm while operators can handle and use devices on the load without unwanted movements of the articulated arm and load. During this stationary mode the suspension system is prepared to react in a predefined way (hold current position or free movement) on unexpected external impacts and/or predicted collisions initiated by movements of other (suspension) systems.

When an operator is pushing/pulling the load with a (optimizable) minimal effort into a desired direction, the suspension system will continue in the move mode during which the load can be repositioned in an easy and smooth way into any desired direction from whatever position of the articulated arm. Also rotating a carrier arm along the stretched position with its main arm is possible.

During repositioning of the load an operator does not have to pay attention to the position of the articulated arm since the brake moments for the first and second rotation connection are dynamically controlled. The suspension system will re-enter the stationary mode if both arms are not rotating anymore after a small period of time.

In an emergency situation an operator can forcefully push away the articulated arm of the suspension system provided with a load without concerning about possible consequences. The first control device is monitoring the speed of repositioning of the load and will, in a controlled way, stop rotations of the articulated arm before the load travels a predefined maximum distance taken into account possible obstacles in the predicted path.

In case a vertical adjustable carrier arm is used in the suspension system the brake moments of the horizontal rotation of the carrier arm are controlled in such a way that this carrier arm will not collide with its main arm during move mode while an actuated vertical movement of the carrier arm will be disabled if a near collision is expected.

If during move mode the rotations of the main arm and/or carrier arm reach their (physical) end stop(s) the brake moments of the related horizontal rotations are controlled in such a way that the rotation is smoothly stopped just before the defined stop position. The presence and replacement of both soft-stop positions (left+right) of rotation connections with a brake device are automatically detected during use of the system.

The predicated space allocation of main arm, carrier arm and load is continuously calculated dynamically and communicated between (suspension) systems in the same room using an allocation space matrix. Also space related information about stationary objects in the room can be stored in the control device. If during move mode a possible collision with a stationary object or other system is expected the control device of the suspension system will control the brake moments of its first and second rotation connection in such a way that collisions of the articulated arm and load are avoided while forcing another path for the load if possible.

For specific applications the suspension system can be equipped with an operator controlled feature to put the articulated arm in a hold/parking mode with all brake moments are at a predefined maximum, or into a manual/override mode in which the controlling functions are disabled with the brake moments at a predefined basic level during which the arms can still be repositioned. After deactivation of these functions the suspension system will enter its stationary mode again.

The rotation connections in a suspension system may have a rotation limiter to avoid damage on the bundle with cables and hoses guided by the system. When using a stop-bolt and one ball in a single slot the maximum rotation freedom of the related arm is less than 360° since over a distance equal to the width of stop-bolt and ball-diameter no rotation is possible. By enlarging the slots to a length equal to a stop-bolt width and two times the ball-diameter, a full rotation over 360° is possible. By placing 1 or 2 balls in one or two slots in the rotation limiter of a rotation connection one can define a limited rotation area for the related arm.

In many cases the articulated arm of a suspension system consists of one main arm and one carrier arm. These articulated arms can be stacked. Additionally a suspension system with double carrier arms is introduced; either below each other at the same rotation axis at the end of the main arm, or at different positions with separate rotation axis and at a different height. In this way it is possible to swing a full functional load from a parking position to an operational position, and back. Examples are:

Two lamp arms below each other at the end of a main arm

One carrier arm with a load to provide gas, power and data to an anesthesia console and a second vertical adjusted carrier arm with a display One carrier arm with facilities for an X-ray shield and a second vertical adjusted carrier arm with a display Dual carrier arm solutions will increase the functionality in an OR, while reducing space occupation in the areas where main arms of other suspension units and other ceiling mounted equipment is located. Furthermore the dual carrier arm offers easier movement of the loads as the main arm is moved only during setup of the room, is locked in place and furthermore during use the (articulated) carrier arms can be moved to position equipment.

A suspension system, with preferably double carrier arms, can be extended with a motorized rotation facility along the first rotation axis of the main arm to rotate the articulated arm within a predefined (adjustable) rotation range.

There are different modes of operation within the same suspension system:

During normal operation the operator is able to initiate, in the stationary mode, using an operator control unit, to direct the main arm to a predefined parking position or one or more predefined application positions. During this actuated rotation the suspension system will be in the move mode.

During normal operation in stationary mode, the first control device is monitoring the shared information about (predicted) space usage of other systems in the same room. If a collision is expected and the suspension system is not in the hold mode, the first control device will direct the motorized rotation facility to rotate the main arm in an opposite direction, within a predefined range, to avoid the collision.

DESCRIPTION OF THE DRAWING

The invention will be discussed in more detail hereinbelow with reference to a drawing in several figures, in which:

FIG. 9-1 shows a cross sectional view of the rotation limiting device according to FIG. 8, using a single first stop element, wherein the rotation limiting device is in its first stop position;

FIG. 9-2 shows a cross sectional view of the rotation limiting device according to FIG. 9-1, wherein the rotation limiting device is in its second stop position;

FIG. 10-1 shows a cross sectional view of the rotation limiting device according to FIG. 8, using two first stop elements, wherein the rotation limiting device is its first stop position;

FIG. 10-2 shows a cross sectional view of the rotation limiting device according to FIG. 10-1, wherein the rotation limiting device is in its second stop position; and FIGS. 11-1, 11-2 and 11-3 show the suspension system according to the invention arranged with double carrier arms.

Similar components are designated in the figure with the same numerals.

DETAILED DESCRIPTION

Figure 1:
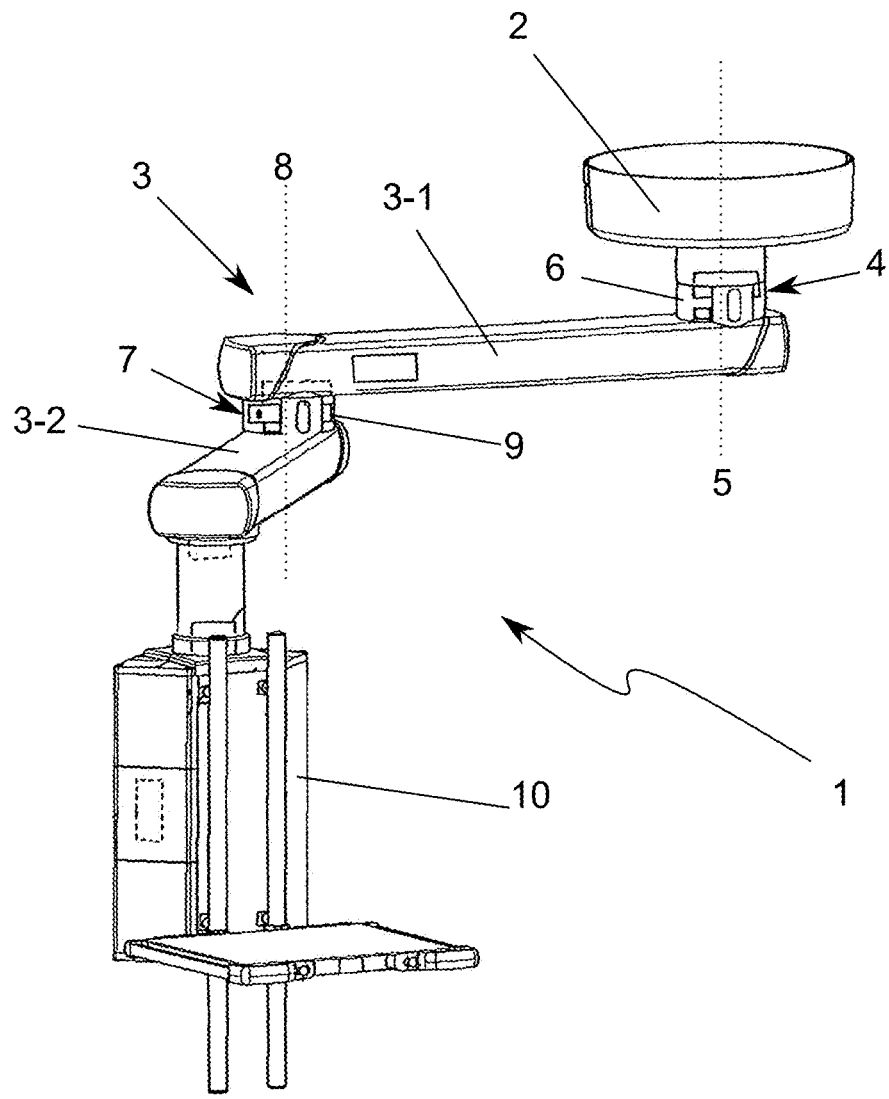
FIG. 1 shows a 3D side view of the known suspension system.

FIG. 1 shows a 3D side view of the known suspension system 1. The known suspension system 1, or stand device 1 or pendant unit 1, is intended for mounting on a ceiling of an operating room for locally moving a load 10, i.e. medical device. The load 10 also generally comprises a carrier frame for carrying the medial device(s). The known suspension system 1 comprises a fastening member 2 for attachment of the suspension system 1 to the ceiling of the operating room (not shown). The suspension system 1 further comprises an articulated arm 3 comprising one main arm 3-1 and a carrier arm 3-2. The proximal end of the main arm 3-1 is connected to the fastening member 2 by means of a first rotation connection 4, which first rotation connection 4 defines a first axis of rotation 5. The main arm 3-1 rotates about the first axis of rotation 4 and in a first plane of rotation. This first plane (not shown) is perpendicular to the first axis of rotation 5. In use of the suspension system 1, the longitudinal direction of the first axis of rotation 5 makes an angle of substantially 90° with the longitudinal plane of the ceiling. The first rotation connection 4 is provided with an electronically operable first brake device 6 for braking the rotation of the main arm 3-1 relative to the first axis of rotation 5. Furthermore, the proximal end of the carrier arm 3-2 is connected to the distal end of the main arm 3-1 by means of a second rotation connection 7. The second rotation connection 7 defines a second axis of rotation 8 for rotating the carrier arm 3-2 about the second axis of rotation 8 and in a second rotation plane. This second plane (not shown) is perpendicular to the second axis of rotation 8. In use of the suspension system 1, the longitudinal direction of the second axis of rotation 8 preferably runs parallel to the longitudinal direction of the first axis of rotation 5. The second rotation connection 7 is provided with an electronically operable second brake device 9 for braking the rotation of the carrier arm 3-2 relative to the second axis of rotation 8. The carrier arm 3-2 is arranged for attaching the load 10 to the proximal end thereof. The suspension system 1 further comprises a first control device for controlling the first and second brake device 6;9. The first control device uses one or more sensors for analyzing an external force acting on the suspension system 1 or a movement produced by the external force and actuating the first and second brake device 6;9.

Figure 2:
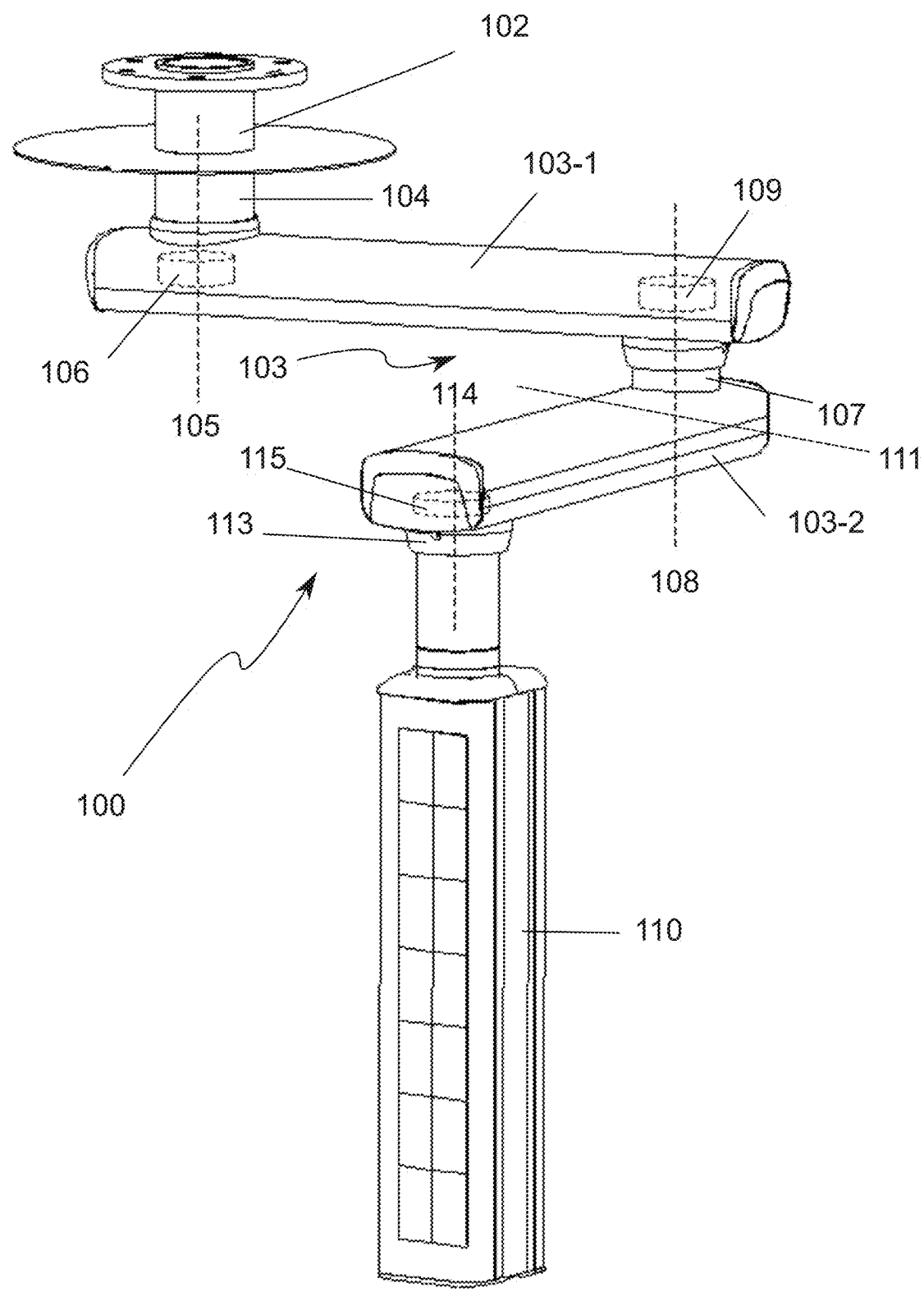
FIG. 2 shows a 3D side view of the suspension system according to the invention.

FIG. 2 shows a 3D side view of the suspension system 100 according to the invention. It is noted that the suspension system according to the invention 100 comprises substantially the same components as the known suspension system 1 as shown in FIG. 1. The components therefore have the same reference number increased with factor 100.

The proximal end of the carrier arm 103-2 comprises a fourth rotation connection (not shown) which is arranged to rotate the carrier arm 103-2 up and down (in use) around the fourth rotation axis 111. In use of the suspension system 100, the fourth rotation axis 111 is substantially horizontal. Preferably the fourth rotation axis 111 and the second rotation axis 108 intersect.

Preferably the distal end of the carrier arm 103-2 comprises a third rotation connection 113 for rotating the load 110 around the third axis of rotation 114, which third axis 114 is, in use of the suspension system 100, substantially parallel to rotation axis 105;108.

The distal end of the carrier arm 103-2 comprises a angle measurement sensor (115) to measure the rotation of the load around the third axis 114.

The first control device and first measuring means are not shown in this Figure.

Figure 3:
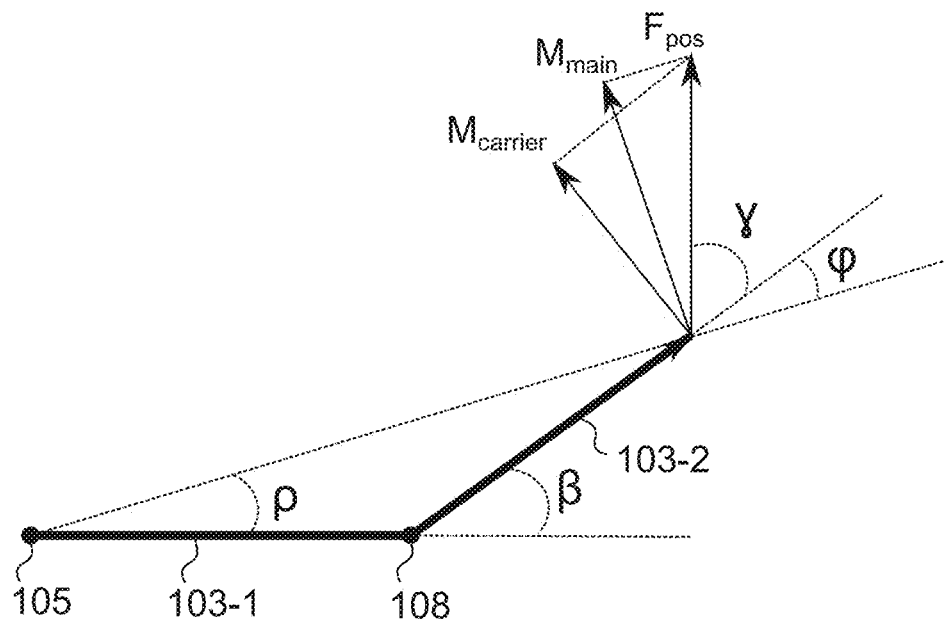
FIG. 3 shows a schematic upper view of the suspension system of FIG. 2 wherein the repositioning force and effective momentums are shown.

FIG. 3 shows a schematic upper view of the suspension system 100 wherein the repositioning force and effective momentums are shown. The horizontal push-pull force ($F_{pos}$) of the user to reposition the load 110 can create an effective momentum $M_{main}$ on the rotation of the main arm (rotating about the first axis 105) and an effective momentum $M_{carrier}$ on the rotation of the carrier arm (rotating around the second axis 108).

These momentums $M_{main}$ and $M_{carrier}$ are dependent on:
the effective lengths of main arm and carrier arm 103-1; 103-2;
the position of carrier arm related to its main arm (β);

the direction (γ) and value of the push-pull force $F_{pos}$ at the end of carrier arm 103-2;

the friction on rotation axis 105;107 due to system parameters and brakes 106;109;

The length of the main arm 103-1 is generally defined as the distance between the first and second axis of rotation 105;108.

The length of the carrier arm 103-2 is generally defined as the distance between the second axis 108 and the third axis of rotation 114 under the condition that the carrier arm 103-2 is in horizontal position.

The reposition force $F_{pos}$ is dynamically and partly allocated to one or both momentums on main arm and carrier arm. The main arm and carrier arm will rotate if the "effective momentum">"friction/brake momentum". The (arm) section 103-1;103-2 of the articulated arm 103 where this happens first will rotate first, and sometimes solely. Problems with the free movement of the load arise when the "Effective momentum" and the "Friction/Brake momentum" on each individual rotation are too far apart. The proposed solution is to:

1. ensure that the "Friction/Brake momentum" of the rotation connection of the main arm follows "Effective momentum" which, among other things, changes due to the angle between main arm and carrier arm.
2. select the "Friction/Brake momentum" of both rotations in such a way that the difference between the controlled "Friction/Brake momentum" and the "Effective momentum" is equivalent so that rotation is possible in every position around every rotation connection. For a horizontal positioning of the load 110 a combined and smooth rotation of both main arm 103-1 and carrier arm 103-2 is required. Smooth rotation of a combination of main arm 103-1 and carrier arm 103-2 can approximately be achieved if rotation of both arms 103-1;103-2 are in harmony. The rotation properties of main arm 103-1 and carrier arm 103-2 during positioning of the load 110 can be influenced by increasing/decreasing the brake-power on their rotation axis 105;108. This can be achieved by:

- measurement of horizontal rotation angles of all arms 103-1;103-2 at their rotation points or axis 105;108, wherein α=angle main arm; β=angle carrier arm; sample period e.g. 0.05 sec; using actual α and β and the moving average of Δα and Δβ over a short period of e.g. 0.1 sec.
- using this information to control the actual brake-power on rotation points 105;107 of all arms 103-1;103-2 with a sample period e.g. 0.1 sec, wherein the reaction speed of electronics and properties of the brake-control are important.
- returning to the stationary values for the desired brake momentum on both rotation connections for the arms; after e.g. 0.5 sec with no significant motion in main arm 103-1 and carrier arm 103-2 of a suspension system.

Figure 4:
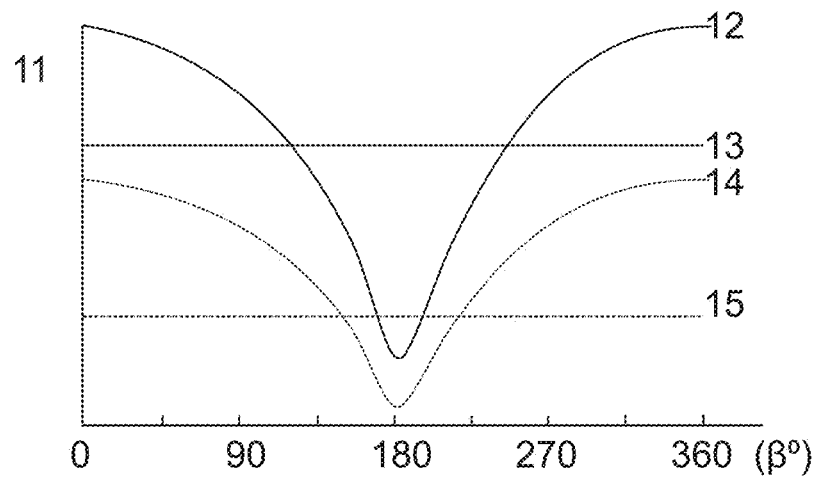
FIG. 4 shows the brake moment of the main arm and the brake moment of the carrier arm in relation to β in stable and in move mode of the suspension system of FIG. 2.

FIG. 4 shows the brake moment of the main arm 103-1 and the brake moment of the carrier arm 103-2 in relation to β in stationary mode and in move mode of the suspension system 100. β is defined as the angle between a longitudinal direction of the main arm 103-1 and the carrier arm 103-2 near the second rotation connection or axis and shown in FIG. 3. On the left vertical axis the absolute value of each brake moment in Nm is displaced. The brake moment of the main arm 103-1 in stationary mode is displayed by line 12. The brake moment of the carrier arm 103-2 in stationary mode is displayed by line 13. In move mode the brake moment of each of the arms 103-1;103-2 is a fraction of the brake moment of each of the arm in stationary mode. The brake moment of the main arm 103-1 in move mode is displayed by line 14. The brake moment of the carrier arm 103-2 in move mode is displayed by line 15. Line 15 shows that the brake moment of the carrier arm 103-2, and therefore the brake friction of the second brake device, will not change significantly over the whole β range. Line 14 shows that the brake moment of the main arm 103-1 can be less or more than the brake moment of the carrier arm 103-2. Subsequently the brake friction of the first brake device can be less or more that the brake friction of the second brake device.

Figure 5:
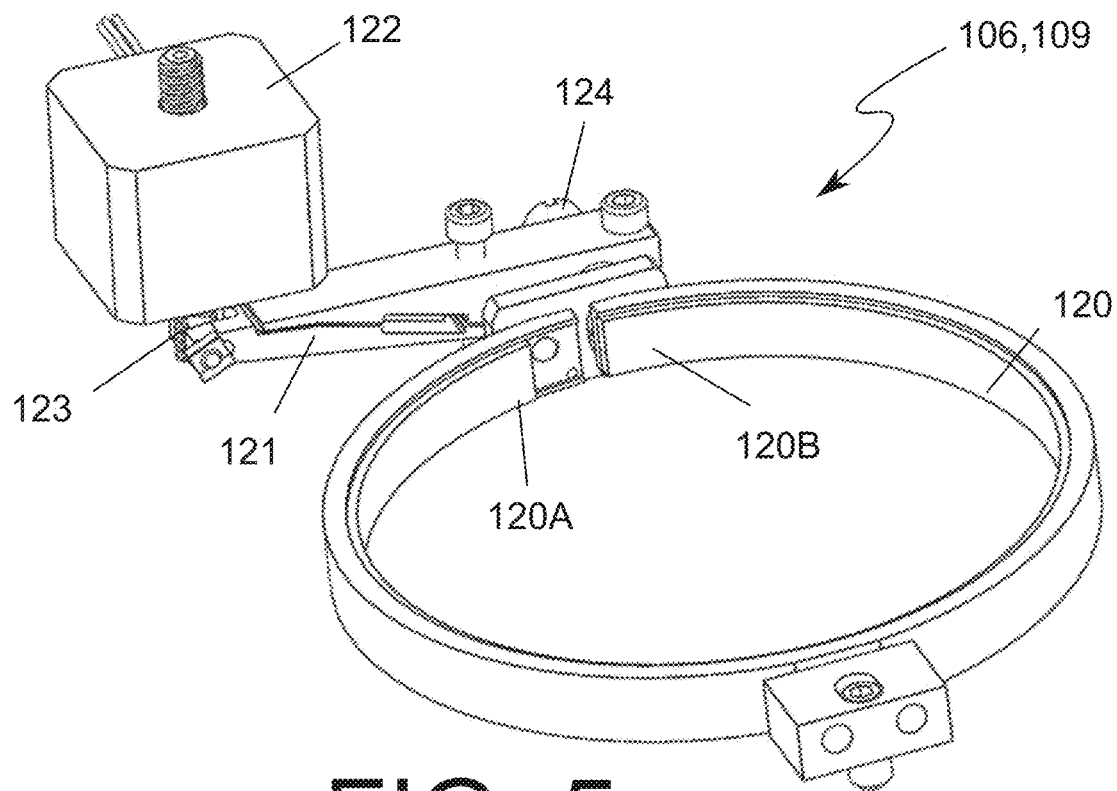
FIG. 5 shows an isometric view of the brake device for use in a suspension system 100 according to the invention.
Figure 6:
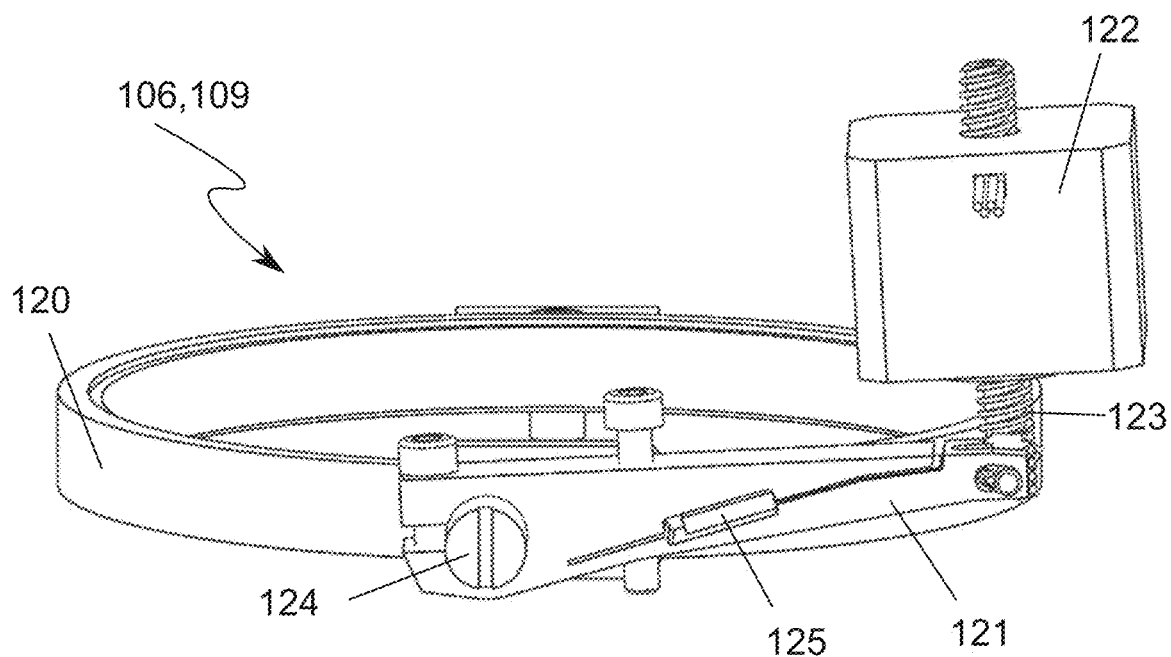
FIG. 6 shows a side view of the brake device of FIG. 5.

FIG. 5 shows an isometric view of the brake device 106;109 for use in a suspension system 100 according to the invention. FIG. 6 shows a side view of the brake device 106;109 of FIG. 5. The brake device 106;109 comprises an at least partially annular brake caliper or brake shoe 120, which caliper 120 is intended for placement over a cylindrical shaped part of the first or second rotation connection 104;107. The inner side of the brake caliper 120 is provided with a brake lining intended for engagement with the rotation connection 104;107. The caliper 120 can be operated by moving the ends 120A;120B of the at least partially annular caliper 120 towards each other by means of a lever 121. The lever 121 is operable by means of a controllable stepper motor 122. A first end of the lever 121 is connected to the ends 120A;120B of the caliper 20 by a rotation point 124. The second end of the lever 121 is connected to the stepper motor 122 by means of a screw thread 123. In operation, the screw thread 123 is powered by the stepper motor 122, which rotates the screw thread 123 is a clockwise and anti-clockwise direction. This rotation causes the lever 121 to rotate around the (adjustable) rotation point 124, causing the ends 120A;120B to move closer or away from each other. The lever 121 is provided with a force sensor 125, and the force exerted on the lever 121 has a predetermined relation with the brake moment.

Due to the design of the brake caliper 120, the output of the force sensor 125 varies with the applied brake torque. The output of the force sensor 125 is also depending on the brake action (increase, decrease, stable) and the rotation of the articulated arm by the operator. The output of force sensor 125 is therefore not always valid.

The brake device 106;109 comprises a second control device (not shown). The second control device comprises an open control for controlling the brake device using the output of the force sensor 125. Internal embedded software of the second control device controls the setting of the (absolute) rotation angle of the motor 122 and therefore the position of the screw thread 123. The absolute position of the screw thread 123 corresponds with a certain brake torque or brake moment. The software comprises a data table wherein the relation between the absolute position of the screw thread 123 and the brake torque is stored, which can be retrieved by the software.

In order to create this table, the following calibration routine is applied. The calibration routine is a controlled activation from a minimal brake torque to a maximal brake torque. This activation is executed in such a way that the output of sensor 125 is known for all applied brake torques.

During startup of the suspension unit 100, the brake force is increased to a defined sensor value. The sensor value is then used to find the position of the screw thread 123 in the said lookup table.

During normal use of the suspension unit 100, the output of sensor 125 is used at certain moments where the conditions allow a reliable sensor reading. The output of sensor 125 is used the check the current applied brake moment or torque. If necessary, a small correction is applied.

Figure 7:
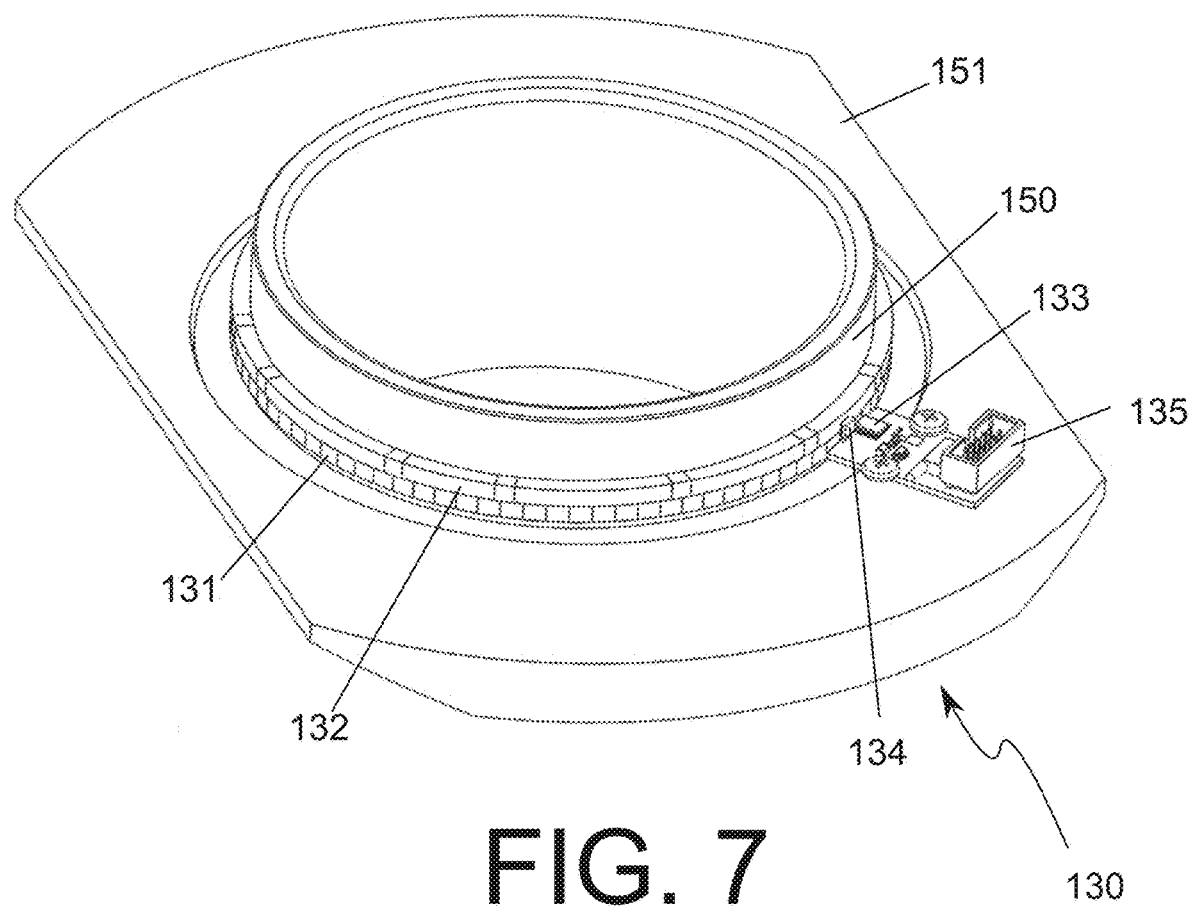
FIG. 7 shows a part of the first measuring means for measuring the angle of rotation and the direction of rotation in a rotation connection.

FIG. 7 shows a part 130 of the first measuring means for measuring the angle of rotation and the direction of rotation in a rotation connection 104;107;113. Part 130 comprises a first magnetic encoder ring 131 and second magnetic encoder ring 132. Both magnetic rings 131; 132 are at a fixed position with respect to each other and both magnetic rings 131; 132 are fixed to the cylindrical shaped part 150 of the rotation connection.

The first magnetic encoder ring 131 has a large number of magnetic pole pairs that are evenly distributed over the circumference of the ring 131. A magnetic sensor 133 fixed to the surrounding part 151 of the rotation connection incrementally measures the passing of the pole pairs of the magnetic ring 131. This determines the relative rotation angle and the rotation speed with the first control device.

The second magnetic encoder ring 132 has a few markers consisting of a few magnetic pole pairs which are all at a different radial distance from each other. The mutual distance between these markers and the position relative to the cylindrical shaped part 150 of the rotation connection are known in the first control device. The magnetic sensor 134, fixed to the surrounding part 151 of the rotation connection, measures the passing of the pole pairs in the markers of magnetic ring 132. After measuring two consecutive markers, the absolute angle position of the cylindrical shaped part 150 with respect to the surrounding part 151 of a rotation connection is therefore known. All generated data is transferred to the first measuring means using the connector 135.

Figure 8:
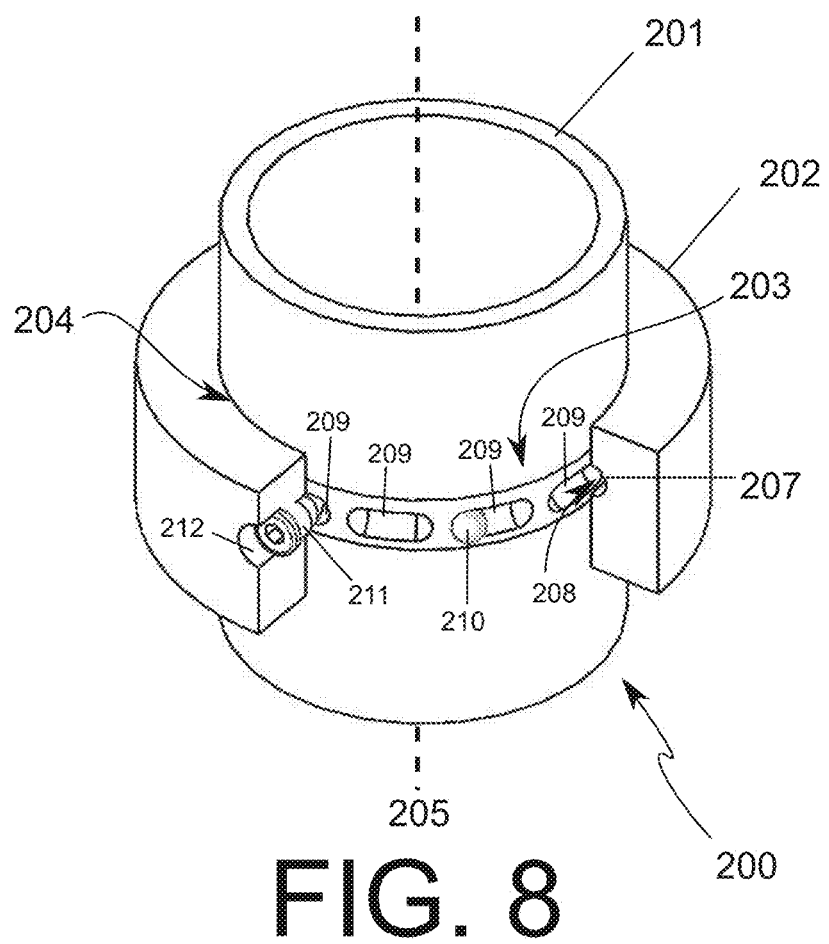
FIG. 8 shows a first embodiment of the rotation limiting device according to the invention.

FIG. 8 shows a first embodiment of the rotation limiting device 200 according to the invention.

The rotation limiting device 200 comprises a first rotation connection member 201 and a second rotation connection member 202, each of which is adapted for further attachment to support a main arm 103-1, support arm 103-2, load 110, carrier or attachment member 102.

The first rotation connection member 201 is provided with a cylindrical shaped part 203. The second rotation connection member 202 is provided with a round recess 204, wherein the cylindrical shaped part 203 is form fittingly arranged. This makes a rotation of first rotation connection member 201 relative to the second rotation connection member 202 about a common axis of rotation 205 possible. Preferably, said rotation is also facilitated by bearings, which are not shown. The round recess 204 of the second rotation connection member 202 is provided with a groove 207 on an inner surface thereof. The cylindrical shaped part 203 and the groove 207 form a hollow space 208 between the first and second rotation connection member 201;203. The cylindrical shaped part 203 is provided with a plurality of slots 209. Each slot 209 partially follows the circumferential direction of the cylindrical shaped part 203 and is adapted to receive a first stop element 210. The first stop element 210 is spherical and extends into the hollow space 208. The slot 209 and the groove 207 have an at least partially circular cross section for fitting the spherical stop element into the hollow space 208. The first stop element 210 is displaceable in the slot 209 during rotation of the first rotation connection member 201 relative to the second rotation connection member 202. The second rotation connection member 202 comprises a second stop element 211. The second stop element 211 is pin-shaped and extends from an outside of the second rotation connection member 202 into the hollow space 208. The second rotation connection 203 is provided with an opening 212 wherein the second stop element 211 can be inserted and fixed. The opening 212 extends from the outer side of the second rotation connection member 203 to an inner side of the groove 207. The opening 212 is wide enough to insert the first stop element 210 into a slot 209. The first stop element 210 is displaceable in the slot over a length of at least twice the width of the portion of the second stop element 211 extending into the hollow space 208. The rotation in a first direction is limited since during rotation the second stop element 211 positions itself against a first side of the first stop element 210 and upon further rotation in the same rotation direction the first stop element 210 by means of the abutting second stop element 211 moves in the slot 209 until a maximum displacement of the first stop element 210 is reached after which further rotation is no longer possible. It is also possible to provide another first stop element in a different slot 209, thereby forming two hard end positions.

Figures 1, 9:
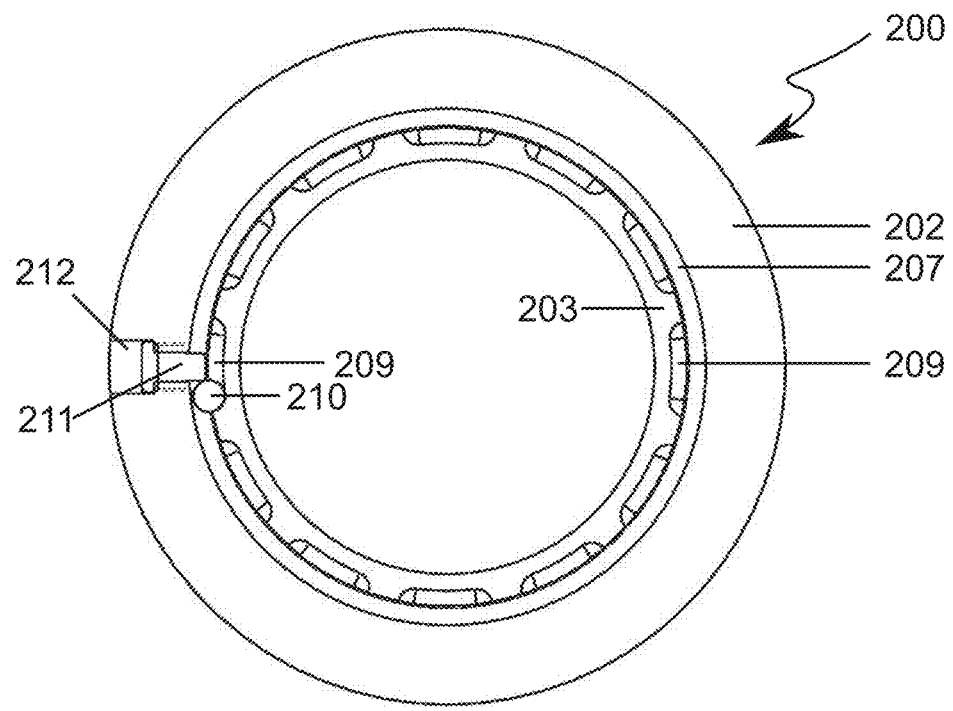
Figures 2, 9:
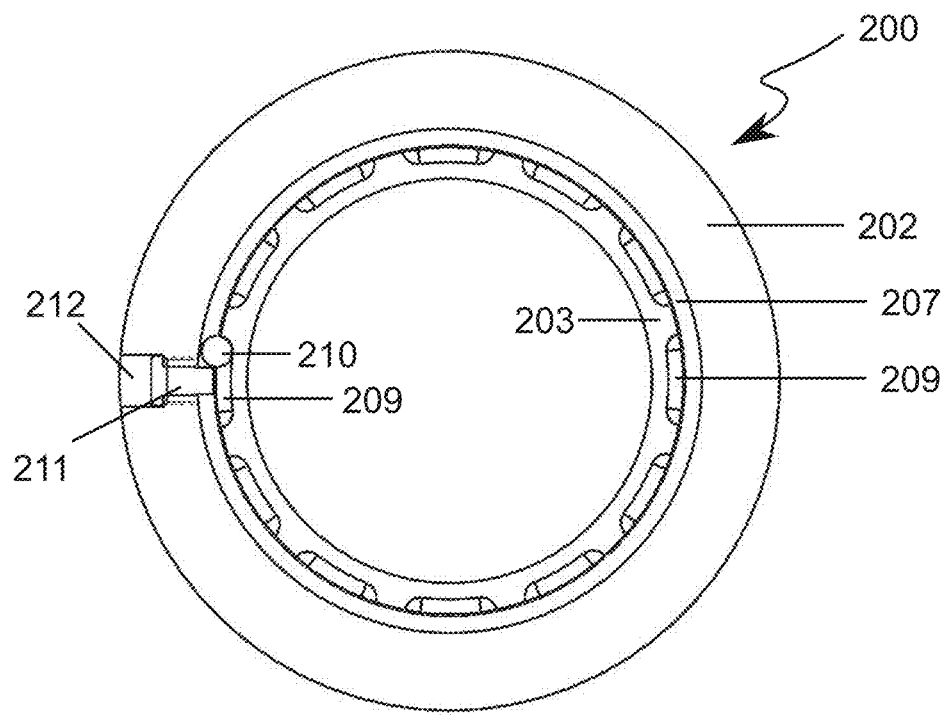

FIGS. 9-1 and 9-2 show a cross-sectional view of the rotation limiting device 200 of FIG. 8, using a single first stop element, wherein the rotation limiting device is its first stop and second stop position.

FIG. 9-1 shows a start position of the rotation of the first rotation connection member 201 relative to the second rotation connection member 202. In the start position a first side of the second stop element 211 abuts a first side of the first stop element 210.

FIG. 9-2 shows an end position of the rotation of the first rotation connection member 201 relative to the second rotation connection member 202. In the end position a second, facing away from the first side, side of the second stop element 211 abuts a second, facing away from the first side, side of the first stop element 210. The first stop element 210 has been displaced to the other side in the slot 209, thereby allowing a full rotation of 360°.

Figures 1, 10:
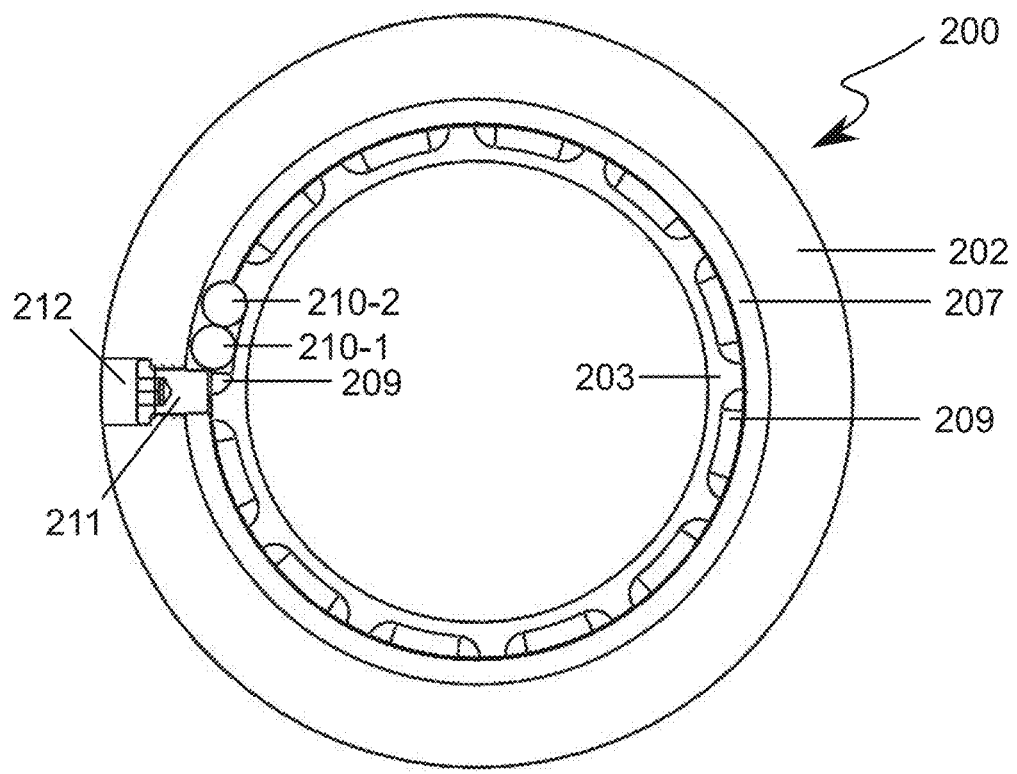
Figures 2, 10:
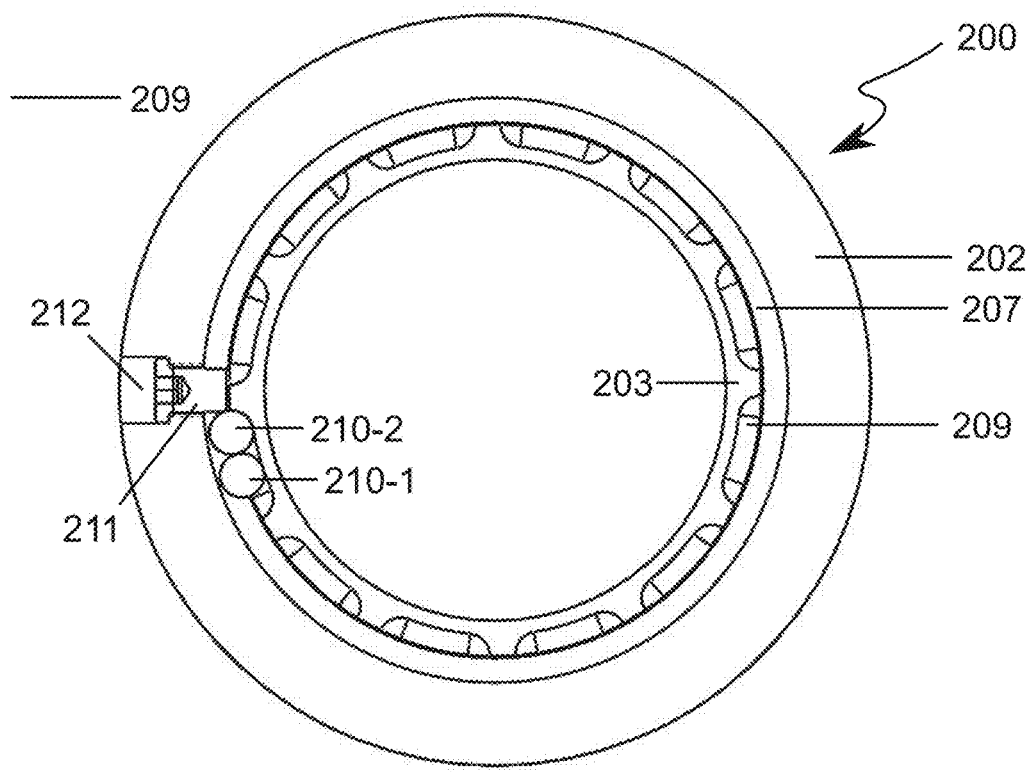

FIGS. 10-1 and 10-2 show a cross-sectional view of the rotation limiting device 200 of FIG. 8 fitted wherein two first stop elements 210-1;210-2 are placed in a single slot 209, wherein FIG. 10-1 shows a start position of the rotation of the first rotation connection member 201 relative to the second rotation connection member 202. In the start position a first side of the second stop element 211 abuts the first stop element 210-1.

FIG. 10-2 shows an end position of the rotation of the first rotation connection member 201 relative to the second rotation connection member 202. In the end position a second, facing away from the first side, side of the second stop element 211 abuts the first stop element 210-2. Compared to FIG. 9-1 and FIG. 9-2, the use of two stop elements allows a more precise definition of the hard rotation stop, but decreases the allowed rotation (<360°).

It is possible to use one or two first stop element placed in different slots to limit the rotation to a certain segment.

The suspension system according to the invention can also be arranged with double carrier arms as shown in FIGS. 11-1, 11-2 and 11-3.

Figures 1, 11:
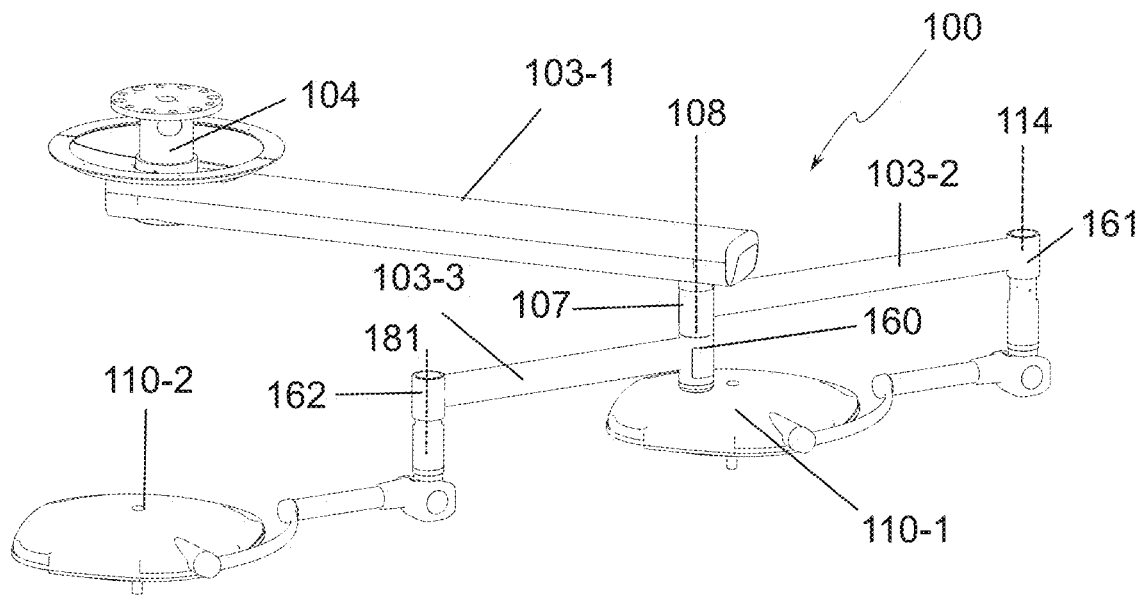
Figures 2, 11:
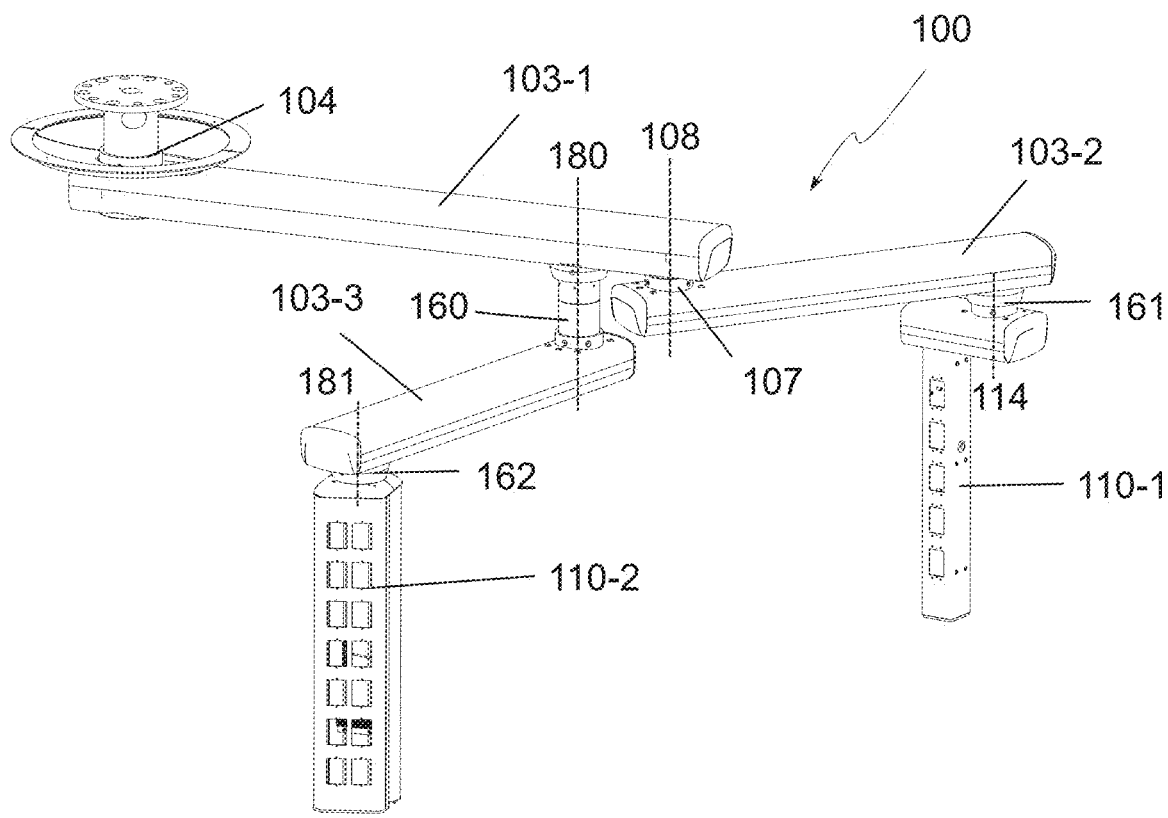
Figures 3, 11:
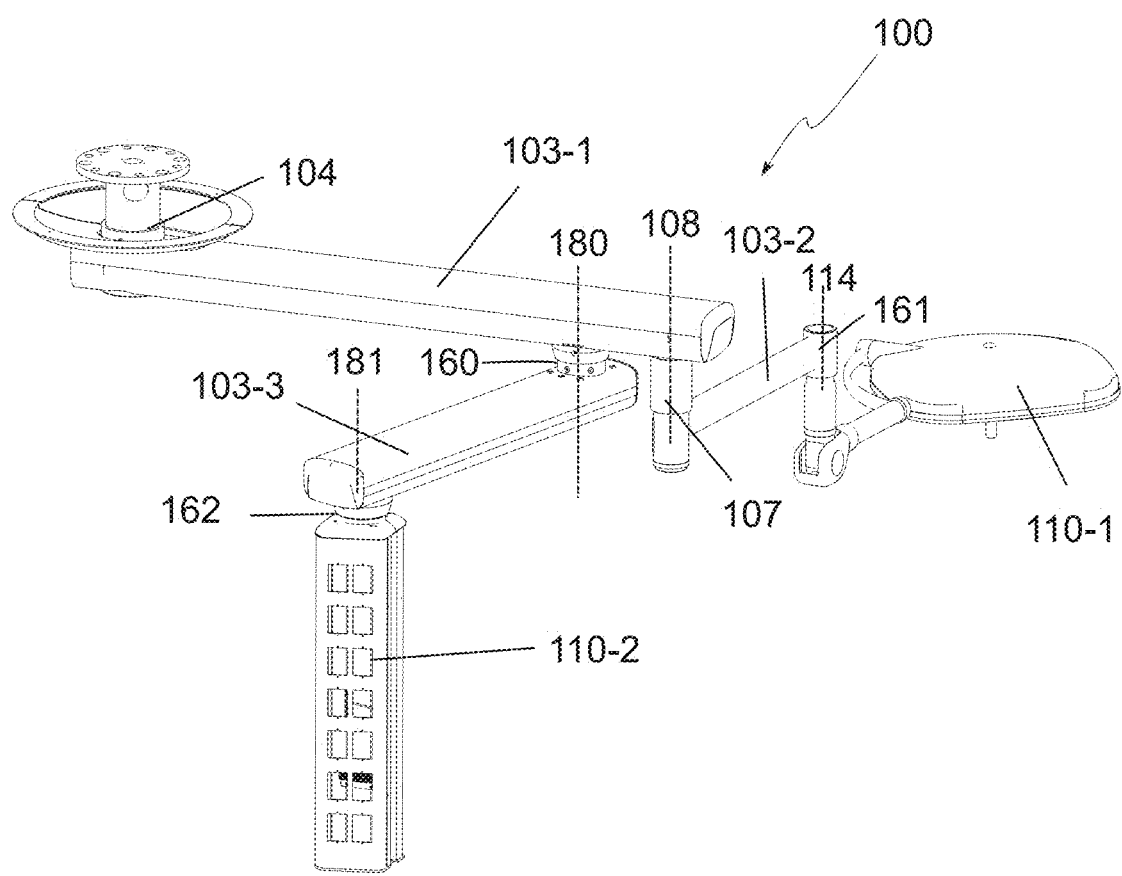

FIG. 11-1 shows a first embodiment of the inventive suspension system 100 with double carrier arms 103-2;103-3. The proximal end of the first and second carrier arm 103-2;103-3 are connected to the distal end of the main arm 103-1 by a separate rotation connection 107;160 along the same rotation axis 108. The angle of rotation of these rotation connections do not coincide. In vertical direction the first carrier arm 103-2 is placed above the second carrier arm 103-3. Both loads 110-1;110-2 of the first and second carrier arm 103-1;103-2 are shown as a lamp, but can be any other type of load.

FIG. 11-2 shows a second embodiment of the inventive suspension system 100 with double carrier arms 103-2;103-3. The proximal end of the first and second carrier arm 103-2;103-3 are connected at different positions to the distal end of the main arm 103-1. Each carrier arm 103-2;103-3 has its own rotation connection 107;160 and rotation axis 108;180. In vertical direction the first carrier arm 103-2 is placed above the second carrier arm 103-3. In this example the rotation angle of the first carrier arm 103-2 is limited by the rotation connection of the second carrier arm 103-3. The load 110-2 of the second carrier arm 103-3 is an equipment carrier provided with one or more electrical, data and gas connections and can rotate around axis 181. The load 110-1 of the first carrier arm 103-2 is also an equipment carrier and can rotate around axis 114.

FIG. 11-2 shows a second embodiment of the inventive suspension system 100 with double carrier arms 103-2; 103-3 in which the first carrier arm 103-2 with load 110-1 in vertical direction is positioned below the second carrier arm 103-3 with load 110-2.

The second carrier arm of the inventive suspension system with double carrier arms can be provided with the same technical features as described for the first carrier arm.

In order to limit the amount of allocated space, the main arm en both carrier arms can be positioned in a parking position, wherein the carrier arms have the same longitudinal direction as the main arm.

By providing a second carrier to the inventive suspension system, the functionality of the suspension system is increased significantly.

In a suspension system according to the invention the rotation connection at the proximal end of the main arm can be equipped with an actuator (e.g. motor) to rotate the main arm to a desired position.

The invention is of course not limited to the described and shown preferred embodiment but extends to any embodiment falling within the scope of protection as defined in the claims and as seen in the light of the foregoing description and accompanying drawings.

The invention claimed is:

1. A suspension system (100) intended for attachment to an upper structure at a selectable height for suspending a load (110) wherein the load (110) may comprise a carrier for one or more medical devices or one or more devices comprising
a fastening member (102) for attachment to the upper structure,
one or more articulated arms (103) comprising a system of one main arm (103-1) and at least one carrier arm (103-2), in which
a proximal end of the main arm (103-1) is connected to the fastening member (102) by means of a first rotation connection (104), which first rotation connection (104) comprises a first axis of rotation (105) for rotating the main arm (103-1) about the first axis of rotation (105) and in a first plane of rotation;
the first rotation connection (104) is provided with an electronically operable first brake device (106) for braking the rotation of the main arm (103-1) relative to the first axis of rotation (105);
a proximal end of the carrier arm (103-2) is connected to a distal end of the main arm (103-1) by means of a second rotation connection (107), which second rotation connection (107) comprises a second axis of rotation (108) for rotating the carrier arm (103-2) about the second axis of rotation (108) and in a second rotation plane;
the second rotation connection (107) is provided with an electronically operable second brake device (109) for braking the rotation of the carrier arm (103-2) relative to the second axis of rotation (108);
the carrier arm (103-2) is arranged for attaching the load (110) to a distal end thereof, by means of a third rotation connection (113);
a first control device for controlling the first brake device (106) and the second brake device (109),
wherein
the suspension system (100) comprises first measuring means for measuring a movement of the articulated arm (103);
the first measuring means are arranged for measuring a first rotation of the main arm (103-1) about the first axis of rotation (105) relative to a predetermined point on the first axis of rotation (105) and measuring a second rotation of the carrier arm (103-2) about the second axis of rotation (108) with respect to the carrier arm (103-2);
the first brake device (106) is controllable by means of an adjustable first brake moment,
the second brake device (109) is controllable by means of an adjustable second brake moment;
the first control device is arranged to dynamically calculate the desired first brake moment and the desired second brake moment on the basis of the actual angle (β) between a longitudinal direction of the main arm (103-1) and the carrier arm (103-2) near the second rotation connection (107) and length of the carrier arm (103-2) and length of the main arm (103-1), in which the relationship between the angle (β) and the first brake moment as well as the relationship between the angle (β) and the second brake moment is predetermined;
the first control device is adapted to control the first brake device (106) and the second brake device (109) to the calculated first and second brake moment respectively wherein, in use of the suspension system (100), the actual first brake moment and actual second brake moment are such that a user will have to exert a minimum displacement force on the load (110) on the load (110) irrespective of a first rotation position of the main arm (103-1) and/or a second rotation position of the carrier arm (103-2);
the first control device is adapted, in use of the suspension system (100), to set the desired first brake moment and the desired second brake moment in stationary state always larger or equal to brake moments wherein the articulated arm (103) moves undesirably due.

2. The suspension system (100) according to claim 1, wherein for stationary placement of the load (110) the first control device is arranged for determining the desired first brake moment, wherein the desired first brake moment is proportional with a first formula:

$$M_{main\ arm,stat} \sim \frac{(F_{min} \times L_{carrier\ arm} \times \sin(\beta))}{\sin\left(arctg\left(\frac{L_{carrier\ arm} \times \sin(\beta)}{L_{main\ arm} + L_{carrier\ arm} \times \cos(\beta)}\right)\right)}$$

and arranged for determining the desired second brake moment for stationary placement of the load (110), wherein the desired second brake moment is proportional with a second formula:

$$M_{carrier\ arm,stat} \sim (F_{min} \times L_{carrier\ arm}) \times Adj(\beta)$$

wherein:

| | | |
|---|---|---|
| $M_{main\ arm,\ stat}$ | = | Desired first brake moment main arm (103-1) at stationary placement of load (110) |
| $M_{carrier\ arm,\ stat}$ | = | Desired second brake moment carrier arm (103-2) at stationary placement of load (110) |
| $F_{min}$ | = | Adjustable minimum displacement force for initial movement of the load (110) |
| $L_{carrier\ arm}$ | = | Length of the carrier arm (103-2) |
| $L_{main\ arm}$ | = | Length of the main arm (103-1) |
| β | = | angle between a longitudinal direction of the main arm (103-1) and the carrier arm (103-2) near the second rotation connection (107) or axis; |
| Adj(β) | = | Dynamic adjusting function based on position of the carrier arm (103-2) (β) to compensate for drift. |

3. The suspension system (100) according to claim 2 wherein the first control device is arranged for controlling the first brake device (106) in move mode, wherein the desired first brake moment is proportional with a third formula:

$$M_{main\ arm,move} \sim M_{main\ arm,stat} \times C(\ )$$

and arranged for controlling the second brake device (109) in move mode wherein the desired second brake moment is proportional with thea fourth formula:

$$M_{carrier\ arm,move} \sim M_{carrier\ arm,stat} \times D(\ )$$

wherein $0 < C(\ ), D(\ ) < 1$ and

| | | |
|---|---|---|
| $M_{main\ arm,\ move}$ | = | Desired first brake moment main arm (103-1) when moving the load (110) |
| $M_{carrier\ arm,\ move}$ | = | Desired second brake moment carrier arm (103-2) when moving the load (110) |
| C( ), D( ) | = | Dynamic control function depending on the state, arm positions and rotation speed of the articulated arm (103). |

4. The suspension system (100) according to claim 3, wherein the parameters C( ) and D( ) have the following values in the different states:
stationary placement of the articulated arm (103): C( ), D( )=1;
moving of the articulated arm (103) by the operator: $0 < C(\ ), D(\ ) < 1$;
locking the articulated arm (103): $1 < C(\ ), D(\ ) < max$, wherein max sets the brake moment to a maximum value;
during unexpected external impacts and control actions to avoid or bypass predicted collisions;
$C(\ ), D(\ ) \neq 1$.

5. The suspension system (100) according to claim 1, wherein the first measuring means comprises the following means for measuring the angle of rotation and the direction of rotation in a rotation connection:
a first and second magnetic encoder ring (131;132) which are placed over a cylindrical shaped part (150) of the first or second rotation connection (104;107), wherein rings (131;132) are rotatable with respect to rotation part (150) when the relevant arm rotates, wherein the first magnetic encoder ring (131) has a large number of magnetic pole pair which are evenly distributed over a circumference of the ring (131) and the second encoder ring (132) has a few markers consisting of a few magnetic pole pairs that are all at a different radial distance from each other wherein the mutual distance between these markers and the position with respect to a cylindrical shaped part (150) of the rotary connection are known in the first control device;
a first magnetic sensor (133) attached to a surrounding part (151) of the rotation connection, which is arranged for step-by-step measuring of passing pole pairs of the magnetic ring (131), to determine the relative rotation angle and the rotation speed;
a second magnetic sensor (134) attached to the surrounding portion (151) of the rotary connection, is arranged for measuring passing pole pairs in markers of the magnetic ring (132) to determine the absolute angular position of the cylindrical shaped member (150) relative to the surrounding member (151) of a rotary joint after measuring two consecutive markers.

6. The suspension system (100) according to claim 1, wherein each rotation connection (104, 107) comprises a rotation-limiting device with a first and/or second (physical) end stop for limiting the rotation between a first physical end angle and a second physical end angle, the first control device is adapted to determine and store the actual values of the first and/or second physical end angle of each rotation connection, and the control device is adapted, in use of the suspension system, when approaching the first respective second end angle of a rotation connection to adjust the braking moment of the brake device of a relevant rotation connection in order to prevent a hard collision with the first respective second end stop, after which the articulated arm enters the stationary mode.

7. The suspension system (100) according to claim 1, wherein
the first control device comprises calculating means for calculating the displacement speed of the load (110) in the move mode on the basis of the first measuring means,
the first control device is arranged to detect the passing of a lower limit value of the speed of movement of a end of the carrier arm (103-2), in which the lower limit value is predetermined,
the first control device is arranged to control the first brake moment and/or second brake moment on detection of the passing of the lower limit value in order to limit the distance travelled by the load (110) to a predefined maximum distance after which the articulated arm (103) is put in stationary mode.

8. The suspension system (100) according to claim 1, wherein
the carrier arm (103-2) is provided near a proximal end with a fourth rotation connection, which fourth rotation connection comprises a fourth rotation axis for rotating the carrier arm (103-2) about the fourth rotation axis in a fourth rotation plane, which fourth plane of rotation is, in use, perpendicular to the second rotation plane;
the first measuring means are arranged for measuring a fourth rotation of the carrier arm (103-2) about the fourth axis of rotation relative to a predetermined point on the fourth axis of rotation;
the first control device is arranged to predict a collision between the carrier arm (103-2) and the main arm (103-1);
the first control device is arranged to increase a second braking moment in the event of a predicted collision and/or to prevent (motorized) movement about the fourth axis of rotation in order to prevent the predicted collision.

9. The suspension system (100) according to claim 1, wherein
the first control device is arranged to calculate and record the actual and predicted allocated space of its own articulated arm (103) and load (110);
the first control device is arranged for storing spatial coordinates of one or more stationary objects not belonging to the suspension system (100) in a space in which articulated arm (103) of the suspension system (100) is movable;
the first control device is arranged to predict a collision of the main arm (103-1) and/or the carrying arm (103-2) and/or load (110) with a stationary object based on the spatial coordinates and the calculated own allocated space;
the first control device is adapted to adjust the first braking moment and/or the second braking moment of the main arm (103-1) and/or carrying arm (103-2) in the event of a predicted collision in order to prevent a collision between the object and the main arm (103-1) and/or carrying arm (103-2) and/or load (110).

10. The suspension system (100) according to claim 1, wherein
the first control device is arranged for communication with one or more further suspension system (100) according to the invention,
the communication comprises information from the (predicted) allocated space of each of the suspension systems that exchange this information with each other,
the first control device is arranged for assessing the own allocated space and the allocated space of one or more further suspension systems for controlling the first and second brake device (106; 109) to prevent a collision between the main arm (103-1), carrying arm (103-2) or load (110) with the main arm (103-1), carrying arm (103-2) or load (110) of the further suspension system (100).

11. A brake device for use in a suspension system (100) intended for attachment to an upper structure at a selectable height for suspending a load (110) wherein the load (110) may comprise a carrier for one or more medical devices or one or more devices comprising
a fastening member (102) for attachment to the upper structure,
one or more articulated arms (103) comprising a system of one main arm (103-1) and at least one carrier arm (103-2), in which
a proximal end of the main arm (103-1) is connected to the fastening member (102) by means of a first rotation connection (104), which first rotation connection (104) comprises a first axis of rotation (105) for rotating the main arm (103-1) about the first axis of rotation (105) and in a first plane of rotation;
the first rotation connection (104) is provided with an electronically operable first brake device (106) for braking the rotation of the main arm (103-1) relative to the first axis of rotation (105);
a proximal end of the carrier arm (103-2) is connected to a distal end of the main arm (103-1) by means of a second rotation connection (107), which second rotation connection (107) comprises a second axis of rotation (108) for rotating the carrier arm (103-2) about the second axis of rotation (108) and in a second rotation plane;
the second rotation connection (107) is provided with an electronically operable second brake device (109) for braking the rotation of the carrier arm (103-2) relative to the second axis of rotation (108);
the carrier arm (103-2) is arranged for attaching the load (110) to a distal end thereof, by means of a third rotation connection (113);
a first control device for controlling the first and second brake device (106;109),
wherein
the suspension system (100) comprises first measuring means for measuring a movement of the articulated arm (103);
the first measuring means are arranged for measuring a first rotation of the main arm (103-1) about the first axis of rotation (105) relative to a predetermined point on the first axis of rotation (105) and measuring a second rotation of the carrier arm (103-2) about the second axis of rotation (108) with respect to the carrier arm (103-2);
the first brake device (106) is controllable by means of an adjustable first brake moment,
the second brake device (109) is controllable by means of an adjustable second brake moment;
the first control device is arranged to dynamically calculate the desired first brake moment and the desired second brake moment on the basis of the actual angle ($\beta$) between a longitudinal direction of the main arm (103-1) and the carrier arm (103-2) near the second rotation connection (107) and length of the carrier arm (103-2) and length of the main arm (103-1), in which the relationship between the angle ($\beta$) and the first brake moment as well as the relationship between the angle ($\beta$) and as the second brake moment is predetermined;
the first control device is adapted to control the first brake device (106) and the second brake device (109) to the calculated first and second brake moment respectively wherein, in use of the suspension system (100), the actual first brake moment and actual second brake moment are such that a user will have to exert a minimum displacement force on the load (110) on the load (110) irrespective of a first rotation position of the main arm (103-1) and/or a second rotation position of the carrier arm (103-2);
the first control device is adapted, in use of the suspension system (100), to set the desired first brake moment and the desired second brake moment in stationary state always larger or equal to brake moments wherein the articulated arm (103) moves undesirably,
wherein
the brake device comprises an at least partially annular brake caliper, which caliper is arranged for placement over a cylindrical shaped part of the first or second rotation connection (107), wherein the inner side of the brake caliper (120) is provided with a brake lining;
the caliper is operable by moving the ends (120A;120B) of the at least partially annular caliper (120) towards each other by means of a lever (121), in which the lever (121) is operable by means of a controllable stepper motor (122) and in which the lever is provided with a force sensor (125),
the force exerted on the lever (121) is a measure for the braking moment of the brake device (106; 109);
the brake device (106; 109) comprises a second control device, which second control device comprises a feedback loop, in which the force sensor (125) is arranged to control the brake device (106; 109) to a desired brake moment as set by the second control device.

12. A rotation limiting device (200) for use in a suspension system (100) intended for attachment to an upper structure at a selectable height for suspending a load (110) wherein the load (110) may comprise a carrier for the one or more medical devices or one or more devices comprising
a fastening member (102) for attachment to the upper structure, one or more articulated arms (103) comprising a system of one main arm (103-1) and at least one carrier arm (103-2), in which a proximal end of the main arm (103-1) is connected to the fastening member (102) by means of a first rotation connection (104), which first rotation connection (104) comprises a first axis of rotation (105) for rotating the main arm (103-1) about the first axis of rotation (105) and in a first plane of rotation;

the first rotation connection (104) is provided with an electronically operable first brake device (106) for braking the rotation of the main arm (103-1) relative to the first axis of rotation (105);

a proximal end of the carrier arm (103-2) is connected to a distal end of the main arm (103-1) by means of a second rotation connection (107), which second rotation connection (107) comprises a second axis of rotation (108) for rotating the carrier arm (103-2) about the second axis of rotation (108) and in a second rotation plane;

the second rotation connection (107) is provided with an electronically operable second brake device (109) for braking the rotation of the carrier arm (103-2) relative to the second axis of rotation (108);

the carrier arm (103-2) is arranged for attaching the load (110) to a distal end thereof, by means of a third rotation connection (113);

a first control device for controlling the first and second brake device (106;109), wherein the rotation limiting device (200) comprises a first rotation connection element (201) and a second rotation connection element (202), each of which is adapted for further attachment to a main arm (103-1), carrying arm (103-2), load (110), carrier or mounting part (102);

the first rotation connection element (201) is at least provided with a cylindrical shaped portion (203), the second rotation connection element (202) is provided with at least a round recess (204), in which the cylindrical shaped portion (203) is fitted in such a way that the first rotation connection element (201) and the second rotation connection element (202) are rotatable relative to each other about a common rotation axis (205);

the round recess (204) of the second rotation connection element (202) is provided with a groove (207) on an inner side all around;

the cylindrical shaped portion (203) and the groove (207) form a hollow enclosed space (208) between the first and second rotary connection element (202);

the cylindrical shaped portion (203) is provided with a plurality of slots (209), wherein each slot (209) partially follows a circumferential direction of the cylindrical shaped portion (203);

each slot (209) is arranged for receiving a first stop element (210), wherein the first stop element (210) extends into the cavity (208) and is movable in the slot (209) during rotation of the first rotation connection element (201) relative to the second rotation connection element (202);

the second rotation connection element (202) comprises one stop elements (211), wherein the second stop element (211) extends at least in the hollow space (208);

wherein the rotation of the first rotation connection element (201) relative to the second rotation connection element (202) in the first rotation direction is limited by a cooperating first and second stop element (211), wherein during rotation the second stop element (211) places itself against a first side of a first stop element (210) and upon further rotation in the first direction of rotation the first stop element (210) moves into the slot (209) by means of the adjacent second stop element (211) until a maximum displacement is reached, after which further rotation is not more is possible.

13. The rotation limiting device (200) according to claim 12, wherein the suspension system (100) comprises first measuring means for measuring a movement of the articulated arm (103);

the first measuring means are arranged for measuring a first rotation of the main arm (103-1) about the first axis of rotation (105) relative to a predetermined point on the first axis of rotation (105) and measuring a second rotation of the carrier arm (103-2) about the second axis of rotation (108) with respect to the carrier arm (103-2);

the first brake device (106) is controllable by means of an adjustable first brake moment, the second brake device (109) is controllable by means of an adjustable second brake moment;

the first control device is arranged to dynamically calculate the desired first brake moment and the desired second brake moment on the basis of the actual angle ($\beta$) between a longitudinal direction of the main arm (103-1) and the carrier arm (103-2) near the second rotation connection (107) and length of the carrier arm (103-2) and length of the main arm (103-1), in which the relationship between the angle ($\beta$) and the first brake moment as well as the relationship between the angle ($\beta$) and the second brake moment is predetermined;

the first control device is adapted to control the first brake device (106) and the second brake device (109) to the calculated first and second brake moment respectively wherein, in use of the suspension system (100), the actual first brake moment and actual second brake moment are such that a user will have to exert a minimum displacement force on the load (110) on the load (110) irrespective of a first rotation position of the main arm (103-1) and/or a second rotation position of the carrier arm (103-2);

the first control device is adapted, in use of the suspension system (100), to set the desired first brake moment and the desired second brake moment in stationary state always larger or equal to brake moments wherein the articulated arm (103) moves undesirably due.

14. The rotation limiting device (200) according to claim 12, wherein the first stop element (210) is displaceable in the slot (209) over a length of at least twice the width of a portion of the second stop element (211) extending into the hollow space.

15. The rotation limiting device (200) according to claim 12, wherein the second rotation connection element (202) is provided with an opening (212) for releasably receiving a second stop element (11), wherein the opening (212) extends from an outside of the second rotary connection element (202) to an inner side of the groove (207) and the opening (212) is arranged for passage of the first stop element (210) to a slot (209).

16. The rotation limiting device (200) according to claim 12, wherein the first stop element (210) is spherical and the slot (209) and the groove (207) have an at least partially circular cross-section for form fitting the spherical stop element into the hollow space (208).

17. The rotation limiting device (200) according to claim 12, wherein the second stop element (211) is pin-shaped.

\* \* \* \* \*